United States Patent
Bosc et al.

(10) Patent No.: US 7,470,719 B2
(45) Date of Patent: Dec. 30, 2008

(54) METASTABLE BENZOXEPNE DERIVATIVES WHICH CAN BE USED IN THE TREATMENT OF DYSLIPIDAEMIA A THEROSCLEROSIS AND DIABETES, PHARMACEUTICAL COMPOSITIONS COMPRISING THEM AND PROCESSES FOR THE PREPARATION THEREOF

(75) Inventors: Nathali Bosc, Montanay (FR); Didier Festal, Ecully (FR); Bernard Boudet, Boudet (FR)

(73) Assignee: Merck Patent GmbH, Darmstadt (DE)

( * ) Notice: Subject to any disclaimer, the term of this patent is extended or adjusted under 35 U.S.C. 154(b) by 269 days.

(21) Appl. No.: 10/530,571

(22) PCT Filed: Sep. 1, 2003

(86) PCT No.: PCT/EP03/09680

§ 371 (c)(1),
(2), (4) Date: Apr. 7, 2005

(87) PCT Pub. No.: WO2004/031166

PCT Pub. Date: Apr. 15, 2004

(65) Prior Publication Data

US 2006/0041007 A1    Feb. 23, 2006

(30) Foreign Application Priority Data

Oct. 7, 2002    (FR) .................................. 02 12432

(51) Int. Cl.
*A01N 43/02*    (2006.01)
*A61K 31/335*    (2006.01)
*C07D 313/00*    (2006.01)

(52) U.S. Cl. ...................................... 514/450; 549/355

(58) Field of Classification Search ................ 549/355; 514/450

See application file for complete search history.

(56) References Cited

U.S. PATENT DOCUMENTS 6,596,758 B1 *    7/2003    Brunet et al. ................ 514/450

FOREIGN PATENT DOCUMENTS

FR    0212432    6/2000
WO    00/39113    *    6/2000

* cited by examiner

*Primary Examiner*—D. Margaret Seaman
*Assistant Examiner*—Niloofar Rahmani
(74) *Attorney, Agent, or Firm*—Millen, White, Zelano & Branigan, P.C.

(57) ABSTRACT

The present invention relates to novel metastable derivatives of benzoxepines of the formula (I) in which n represents 0, 1 or 2; and the radicals R, which may be identical or different, are alkyl or alkoxy groups, or halogen atoms, which can be used in the treatment of dyslipidaemia, atherosclerosis and diabetes.

14 Claims, 6 Drawing Sheets

METASTABLE BENZOXEPNE DERIVATIVES WHICH CAN BE USED IN THE TREATMENT OF DYSLIPIDAEMIA ATHEROSCLEROSIS AND DIABETES, PHARMACEUTICAL COMPOSITIONS COMPRISING THEM AND PROCESSES FOR THE PREPARATION THEREOF

The invention relates to a process for obtaining the metastable form of 2E,4E-5-(3,3-dimethyl-2,3-dihydro-1-benzoxepin-5-yl)-3-methylpentadien-2,4-oic acid and a number of its derivatives, and also to the corresponding metastable forms of these compounds, per se.

2E,4E-5-(3,3-Dimethyl-2,3-dihydro-1-benzoxepin-5-yl)-3-methylpentadien-2,4-oic acid has the formula:

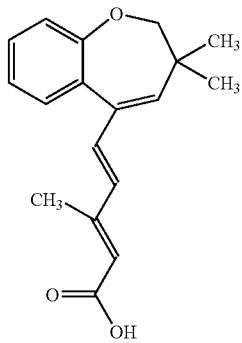

The derivatives of this acid that are targeted by the invention are those in which the phenyl group is substituted by one or two substituents chosen from alkyl, alkoxy and a halogen atom.

The compound of the formula A:

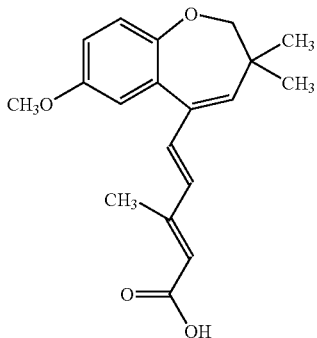

A is especially disclosed in FR 98 16 574, in Example 16 (compound 16b).

This compound was isolated according to FR 98 16 574 in its stable form.

According to the said document, the acid A in stable form is prepared from a corresponding alkyl ester of the formula B:

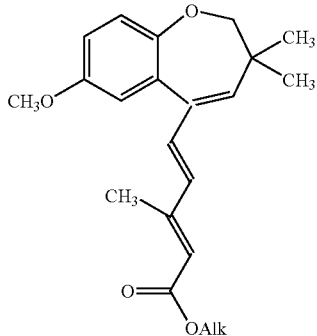

B in which Alk represents $C_1$-$C_6$ lower alkyl, by saponification, acidification of the reaction medium and extraction, followed by crystallisation from an organic solvent, such as ethyl acetate.

Other solvents that can be used to recrystallise the acid A in its stable form are acetonitrile, methanol, tetrahydrofuran, tert-butyl methyl ether, acetone, ethanol and 2-propanol.

The invention provides a process for obtaining the metastable forms of compounds of the formula I

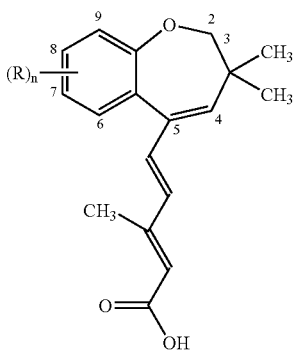

I in which
  n represents 0, 1 or 2;
  and the radicals R, which may be identical or different, are alkyl or alkoxy groups or halogen atoms.

In point of fact, the metastable crystalline form is of significant advantage in terms of pharmaceutical presentation, especially in the case of a presentation form comprising a high dose of active principle.

The process of the invention more specifically comprises the steps consisting in:
  a) salifying the corresponding stable form of the compound of the formula I by forming a carboxylic acid salt;
  b) acidifying an aqueous solution of the salt obtained after step a) until precipitation of the carboxylic acid in its metastable form is obtained.

The stable form of the compound of the formula I can be prepared simply by performing the steps consisting in:
  saponifying, preferably by the action of sodium hydroxide or potassium hydroxide, at a temperature from 50 to 110° C., for example at a temperature from 60 to 85° C., an alkyl ester of 2E,4E-5-(3,3-dimethyl-2,3-dihydro-1-benzoxepin-5-yl)-3-methylpentadien-2,4-oic acid;
  acidifying the resulting reaction medium;
  extracting the acid obtained by adding a water-immiscible solvent, for instance an ether or an ester, such as ethyl acetate,
  evaporating off the solvent;
  crystallising from a solvent chosen from a lower alkanol, acetonitrile, ethyl acetate, tetrahydrofuran and acetone.

Examples of lower alkanols include $C_1$-$C_4$ alcohols, such as methanol, ethanol and propanol.

In step a), the salification can be performed with any organic or mineral base generally used in the art.

The salification step can thus give a salt of an alkali metal, of an alkaline-earth metal or of a transition metal (such as sodium, potassium, calcium, magnesium or aluminium).

The salification is preferably performed by the action of sodium hydroxide or potassium hydroxide, to give the corresponding sodium or potassium salt, respectively.

According to one preferred embodiment of the invention, the salt is not isolated from the reaction medium. Thus, it is desirable to perform the process of step a) in aqueous medium.

Advantageously, in step a), a mineral or organic base is added to a suspension of the acid of the formula I or a derivative thereof in water.

The addition of the base is preferably performed at a temperature of between 10 and 30° C. and better still between 15 and 20° C.

The acid concentration at the start of the addition of the base usually ranges between 0.1 and 5 M and better still between 0.1 and 1 M, for example between 0.5 M and 1 M.

According to one preferred embodiment of the invention, the reaction medium is filtered through filter paper or a sinter funnel and the filter is then rinsed with water, which is combined with the filtrate.

Step b) is then performed using this filtrate.

In step b), any acid usually used to release a carboxylic function in salt form can be used for the acidification. Examples of acids that can be used are, for example, hydrochloric acid, hydrobromic acid, a sulfuric acid, a phosphoric acid, a sulfonic acid, citric acid, maleic acid and fumaric acid.

The acid used for the acidification is preferably hydrochloric acid or sulfuric acid.

According to the preferred embodiment of the invention described above, the acid is added directly to the aqueous reaction medium comprising the salt and obtained directly in step a), without intermediate isolation of the salt.

As a variant, the salt obtained in step a) is isolated and then redissolved in an aqueous solution consisting essentially of water before addition of the acid, for example before addition of hydrochloric acid or sulfuric acid.

The acidification is usually performed at a temperature from 50 to 120° C. and preferably at a temperature of between 70 and 90° C.

The concentration of carboxylic acid of the formula I preferably ranges between 0.05 and 10 M and preferentially between 0.1 and 0.5 M at the end of the acidification.

The invention also relates to the metastable form of the compounds of the formula I resulting from the process of the invention:

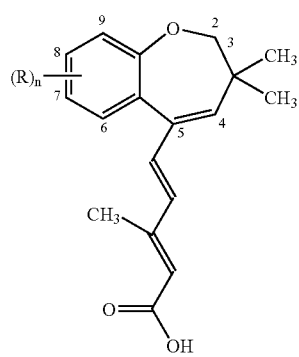

I in which:

n represents 0, 1 or 2;

and the radicals R, which may be identical or different, are alkyl or alkoxy groups or halogen atoms.

A preferred metastable form that may be mentioned is that of the compound of the formula I in which n=1 and R, in position 7, represents methoxy.

Figure 1:
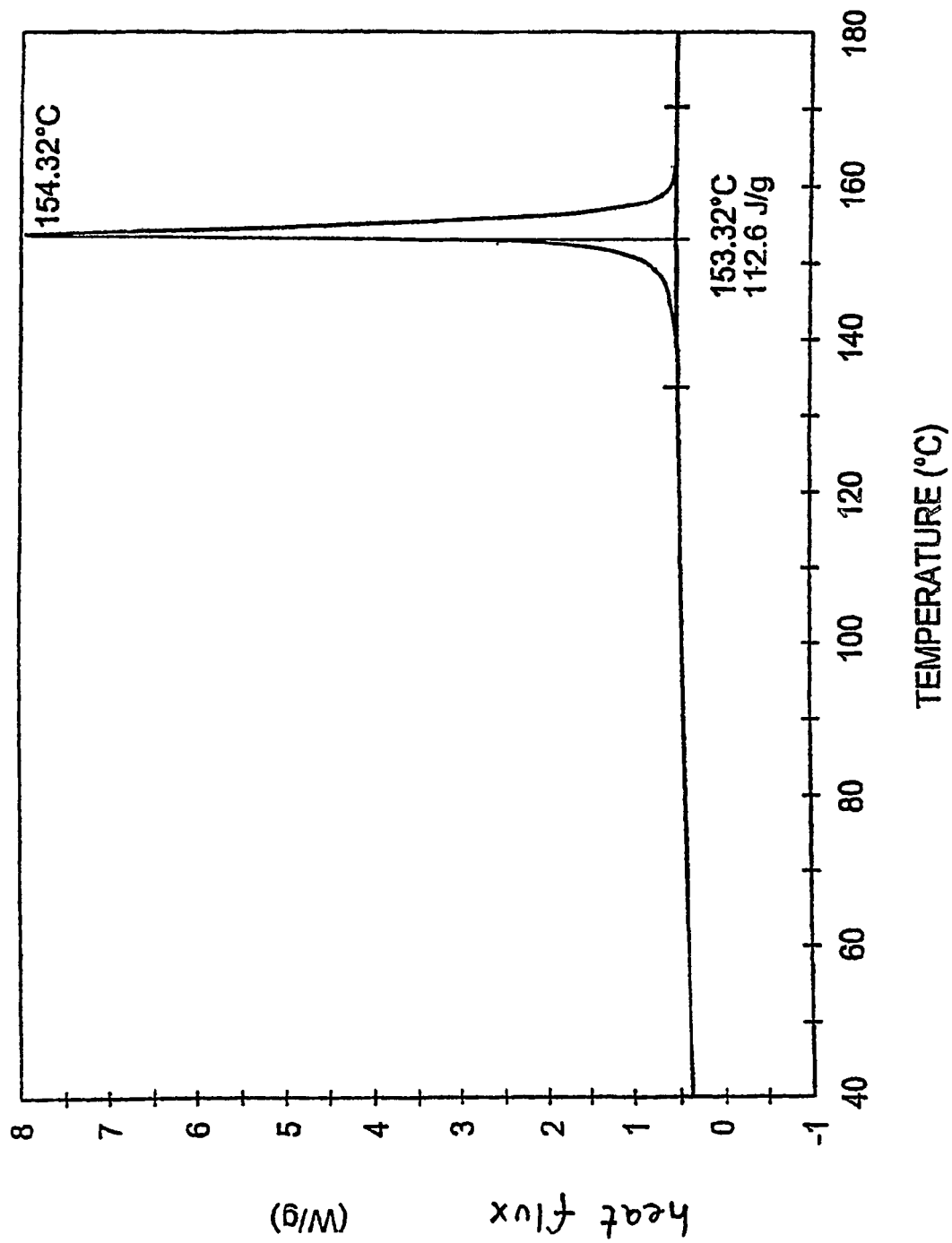
FIG. 1 represents differential thermal analysis of a compound of formula I in which n is 1 and R is methoxy.

The metastable form of the compound of the formula I in which n represents 1 and R, in position 7, represents methoxy is also characterised by:

a melting point of 151 to 153° C. as measured by differential thermal analysis by scanning between 40 and 180° C. at a rate of 0.5° C./minute; the curve obtained by differential thermal analysis is shown in FIG. 1;

an IR absorption spectrum, shown in FIG. 2, and defined by the absorption wavelengths in Table I below:

| No. | Absorption wavelength (cm$^{-1}$) | Percentage of transmission (%) | Intensity |
| --- | --- | --- | --- |
| 1 | 620.27 | 0.660 | m |
| 2 | 644.38 | 0.892 | w |
| 3 | 679.11 | 0.865 | w |
| 4 | 709.98 | 0.568 | m |
| 5 | 730.24 | 0.907 | w |
| 6 | 736.03 | 0.891 | w |
| 7 | 745.67 | 0.849 | w |
| 8 | 761.11 | 0.843 | w |
| 9 | 814.16 | 0.518 | m |
| 10 | 839.24 | 0.683 | m |
| 11 | 849.85 | 0.889 | w |
| 12 | 869.15 | 0.660 | m |
| 13 | 878.79 | 0.466 | s |
| 14 | 899.05 | 0.936 | w |
| 15 | 925.10 | 0.755 | m |
| 16 | 951.14 | 0.740 | m |
| 17 | 966.58 | 0.688 | m |
| 18 | 973.33 | 0.587 | m |
| 19 | 987.80 | 0.815 | w |
| 20 | 1028.31 | 0.641 | m |
| 21 | 1046.64 | 0.517 | m |
| 22 | 1052.43 | 0.562 | m |
| 23 | 1064.97 | 0.859 | w |
| 24 | 1128.64 | 0.825 | w |
| 25 | 1168.19 | 0.797 | w |
| 26 | 1190.37 | 0.422 | s |
| 27 | 1199.06 | 0.408 | s |
| 28 | 1212.56 | 0.441 | s |
| 29 | 1251.15 | 0.442 | s |
| 30 | 1270.44 | 0.254 | s |
| 31 | 1295.52 | 0.659 | m |
| 32 | 1318.67 | 0.825 | w |
| 33 | 1355.33 | 0.769 | w |

-continued

Figure 3:
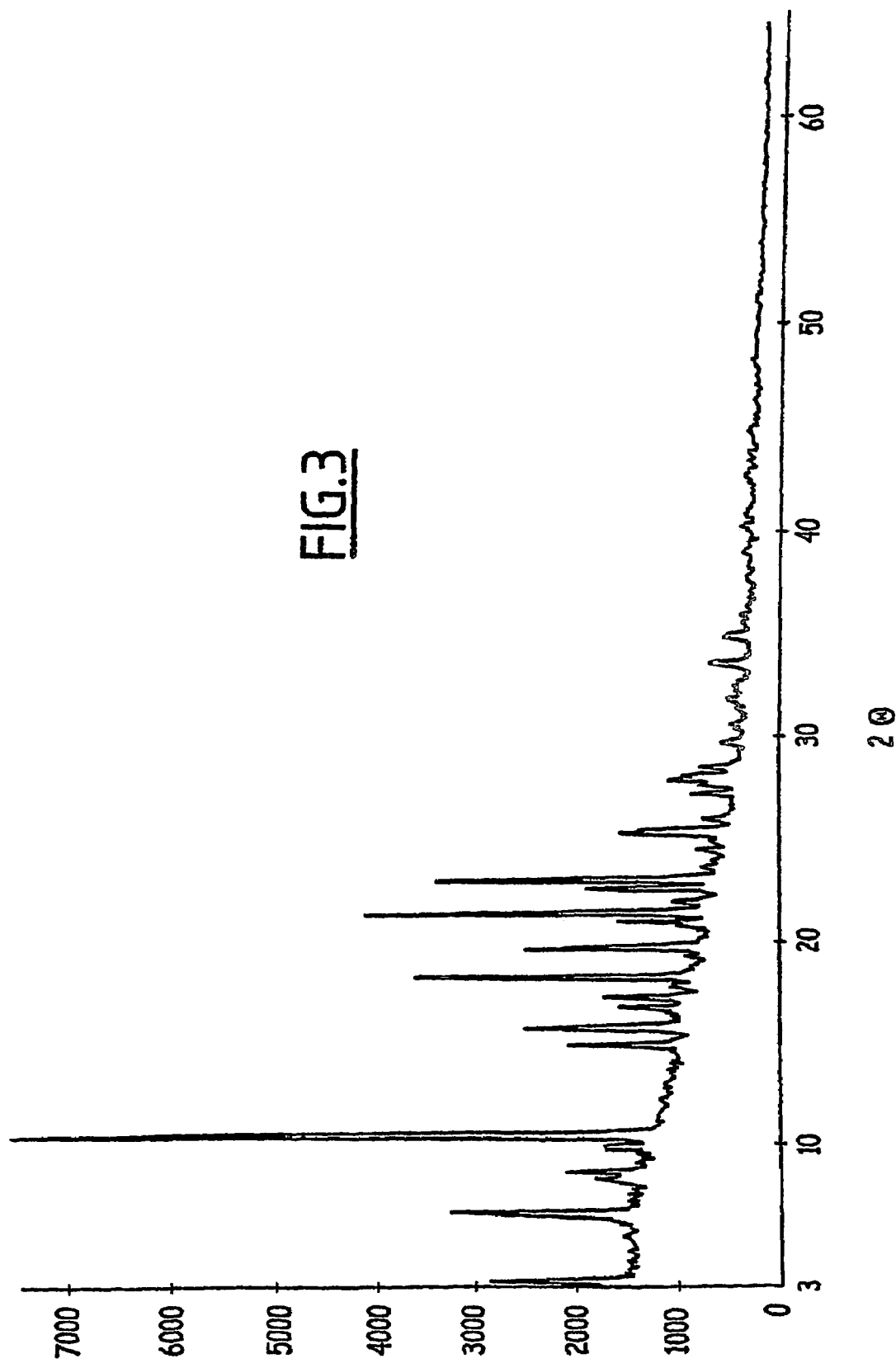
FIG. 3 represents an X-ray defraction spectrum of the compound of FIG. 1.

| No. | Absorption wavelength (cm$^{-1}$) | Percentage of transmission (%) | Intensity |
|---|---|---|---|
| 34 | 1391.98 | 0.872 | w |
| 35 | 1393.91 | 0.872 | w |
| 36 | 1413.21 | 0.651 | m |
| 37 | 1432.50 | 0.806 | w |
| 38 | 1464.33 | 0.743 | m |
| 39 | 1494.24 | 0.511 | m |
| 40 | 1572.37 | 0.707 | m |
| 41 | 1599.38 | 0.284 | s |
| 42 | 1623.50 | 0.810 | w |
| 43 | 1663.05 | 0.650 | m |
| 44 | 1676.55 | 0.458 | s |
| 45 | 2837.99 | 0.863 | w |
| 46 | 2871.75 | 0.847 | w |
| 47 | 2934.45 | 0.819 | w |
| 48 | 2960.50 | 0.818 | w |
| 49 | 3018.38 | 0.898 | w | in which
w means weak intensity,
s means strong intensity, and
m means medium intensity;

an X-ray diffraction spectrum as shown in FIG. 3.

The invention also relates to pharmaceutical compositions comprising, as active principle, the metastable form of a compound of the formula I as defined above, in combination with a pharmaceutically acceptable excipient.

These compositions can be administered orally in the form of tablets gel capsules or granules with immediate release or sustained release, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrating agent, a lubricant, a colorant or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, acacia, gum tragacanth, gelatine, shellac, hydroxypropylcellulose, hydroxypropylmethylcellulose, calcium citrate, dextrin and pectin. Examples of lubricants include magnesium stearate, talc, polyethylene glycol, silica and hardened plant oils. The colorant may be any of those permitted for used in medicaments. Examples of flavour enhancers include cocoa powder, mint in herb form, aromatic powder, mint in oil form, borneol and cinnamon powder. Obviously, the tablet or granule may be suitably coated with sugar, gelatine or the like.

An injectable form comprising the compound of the present invention as active principle is prepared, where appropriate, by mixing the said compound is with a pH regulator, a buffer agent, a suspension agent, a solubiliser, a stabiliser, an isotonic agent and/or a preserving agent, and by converting the mixture into a form for intravenous, subcutaneous or intramuscular injection, according to a standard process. Where appropriate, the injectable form obtained can be freeze-dried by a standard process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilisers include castor oil solidified with polyoxyethylene, polysorbate 80, nicotinamide, polyethoxylated sorbitan monolaurate and the ethyl ester of castor oil fatty acid.

In addition, the stabiliser encompasses sodium sulfite, sodium metasulfite and ether, while the preserving agent encompasses methyl p-hydroxybenzoate, ethyl p-hydroxybenzoate, sorbic acid, phenol, cresol and chlorocresol.

According to another of its aspects, the invention relates to the use of the metastable form of a compound of the formula I as defined above, for the preparation of a medicament for the prevention or treatment of dyslipidaemia, atherosclerosis and diabetes.

The invention is also illustrated by the two implementation examples that follow, describing the preparation of each of the stable and metastable forms of the compound of the formula I in which n represents 1 and R, in position 7, represents methoxy.

m.p. denotes the melting point.

COMPARATIVE EXAMPLE 1

Preparation of the Stable Form of 2E, 4E-5-(3,3-dimethyl-2,3-dihydro-1-benzoxepin-5-yl)-3-methyl-pentadien-2,4-oic Acid 1.9 kg of crude ethyl 2E,4E-(methoxy-7-dimethyl-3,3-dihydro-2,3-benzoxepin-1-yl-5)-5-methyl-3-pentadien-2,4-oate (compound 16a of patent application FR 98 16 574) are dissolved in 8.8 l of methanol, 8.8 l of water and then 0.6 l of caustic soda are added thereto and the heterogeneous mixture thus obtained is refluxed (78° C.) with stirring for two hours. Next, the orange solution obtained is evaporated until a temperature of 90° C. is reached, it is then cooled to about 45° C. and 8 l of tert-butyl methyl ether are added, followed by addition of 0.7 l of 37.5% sulfuric acid. The mixture is stirred for 15 minutes between 40 and 45° C. and the organic phase is then separated out by settling, washed at this same temperature with twice 5 l of water and then filtered, and the filtrate is distilled at normal pressure. When the reaction medium begins to crystallise, 12 l of acetonitrile are added thereto, followed by removal by distillation at normal pressure of 6.5 l of the acetonitrile/tert-butyl methyl ether extraction mixture and the remaining mixture is cooled to about 25° C. over 1 hour 30 minutes and then to about 10° C., at which temperature it is stirred for two hours. The precipitate obtained is filtered off by suction and washed successively with twice 1 l of fresh acetonitrile and then with twice 2 l of water, and is dried in a ventilated oven at 60° C.

Mass obtained: 1.35 kg (theoretical: 1.764 kg)

yield=82.3% m.p.=157.3° C. (as measured on a Büchi machine)

HPLC: purity of 99.89%

The melting point as measured by differential thermal analysis is 156° C. It was measured by scanning in the temperature interval ranging from 20° C. to 180° C., at a rate of temperature increase of 10° C./minute.

Figure 4:
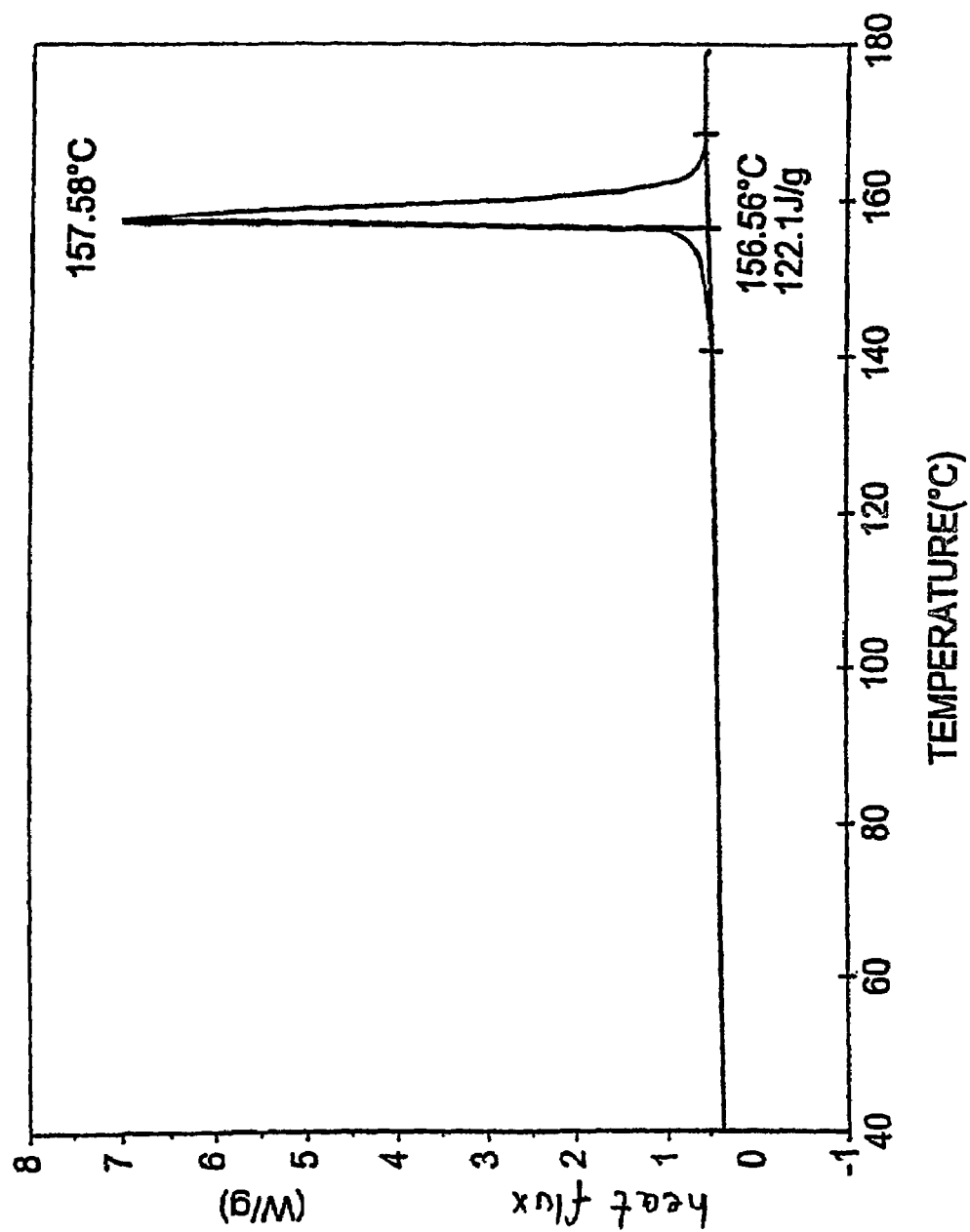
FIG. 4 represents differential thermal analysis of a compound produced in comparative example 1.

The curve of the differential thermal analysis is given FIG. 4.

Figure 5:
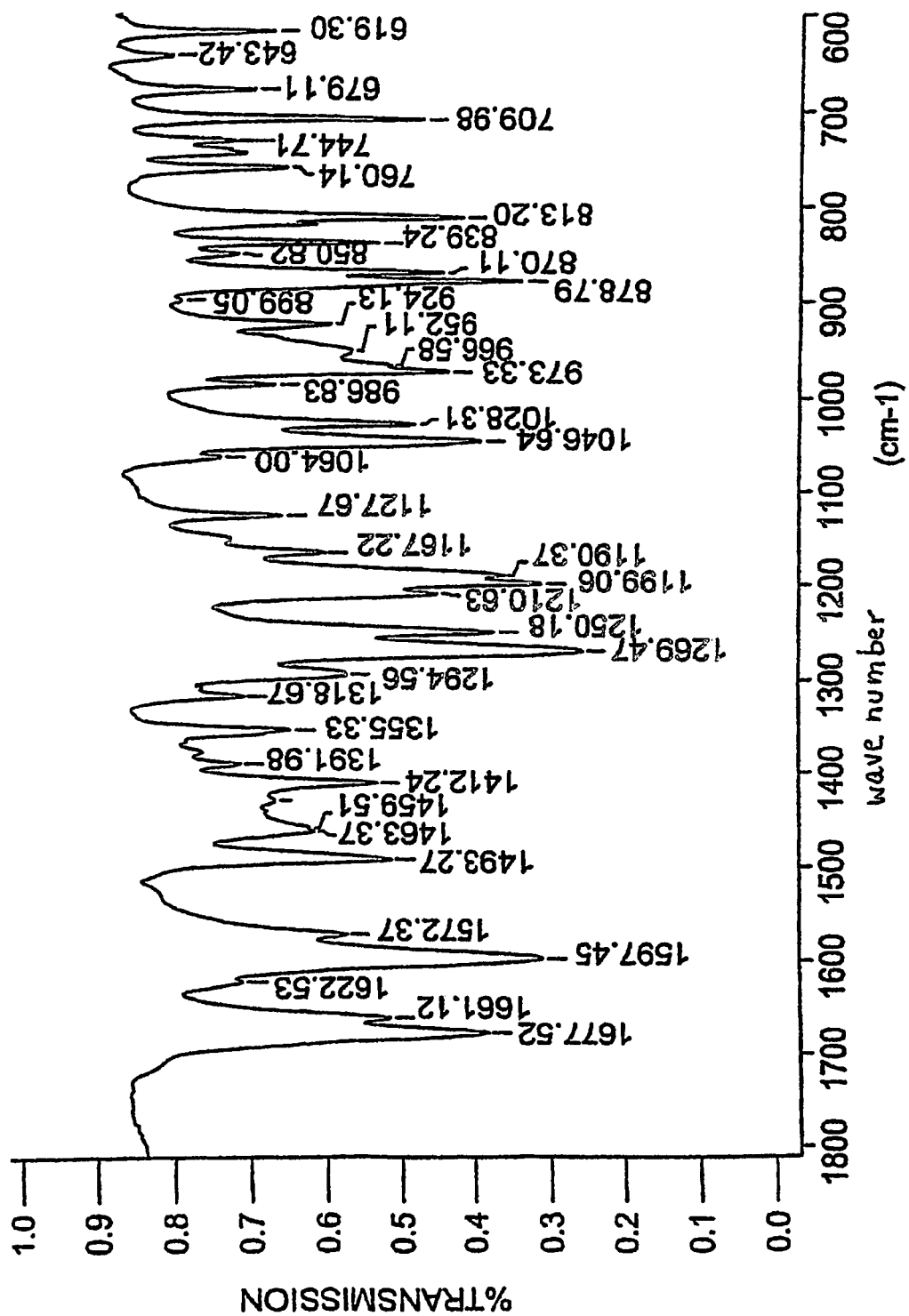
FIG. 5 represents an IR spectrum of the comparative compound of FIG. 4.

FIG. 5 shows the IR spectrum of the stable form obtained.

The characteristics wavelengths of the IR absorption spectrum of the stable form are given in Table II below:

TABLE II

| No. | Wavelength (cm$^{-1}$) | Percentage of transmission (%) | Intensity |
|---|---|---|---|
| 1 | 619.30 | 0.674 | m |
| 2 | 643.42 | 0.810 | m |
| 3 | 679.11 | 0.699 | m |
| 4 | 709.98 | 0.473 | s |
| 5 | 731.20 | 0.725 | m |
| 6 | 740.85 | 0.729 | m |

TABLE II-continued

| No. | Wavelength (cm⁻¹) | Percentage of transmission (%) | Intensity |
|---|---|---|---|
| 7 | 744.71 | 0.709 | m |
| 8 | 760.14 | 0.655 | m |
| 9 | 813.20 | 0.418 | s |
| 10 | 819.95 | 0.616 | s |
| 11 | 839.24 | 0.532 | s |
| 12 | 850.82 | 0.720 | m |
| 13 | 870.11 | 0.445 | s |
| 14 | 878.79 | 0.337 | vs |
| 15 | 899.05 | 0.794 | m |
| 16 | 924.13 | 0.596 | s |
| 17 | 952.11 | 0.567 | s |
| 18 | 966.58 | 0.516 | s |
| 19 | 973.33 | 0.436 | s |
| 20 | 986.83 | 0.670 | m |
| 21 | 1028.31 | 0.482 | s |
| 22 | 1046.64 | 0.391 | s |
| 23 | 1064.00 | 0.740 | m |
| 24 | 1127.67 | 0.660 | m |
| 25 | 1167.22 | 0.604 | s |
| 26 | 1190.37 | 0.362 | s |
| 27 | 1199.06 | 0.311 | vs |
| 28 | 1210.63 | 0.452 | s |
| 29 | 1250.18 | 0.373 | s |
| 30 | 1269.47 | 0.257 | vs |
| 31 | 1294.56 | 0.573 | s |
| 32 | 1318.67 | 0.710 | m |
| 33 | 1355.33 | 0.648 | s |
| 34 | 1391.98 | 0.715 | m |
| 35 | 1412.24 | 0.534 | s |
| 36 | 1431.53 | 0.668 | m |
| 37 | 1459.51 | 0.624 | s |
| 38 | 1463.37 | 0.618 | s |
| 39 | 1493.27 | 0.514 | s |
| 40 | 1572.37 | 0.574 | s |
| 41 | 1597.45 | 0.310 | vs |
| 42 | 1622.53 | 0.711 | m |
| 43 | 1661.12 | 0.515 | s |
| 44 | 1677.52 | 0.383 | s |
| 45 | 2837.99 | 0.689 | m |
| 46 | 2870.79 | 0.675 | m |
| 47 | 2932.52 | 0.643 | s |
| 48 | 2959.53 | 0.652 | s |
| 49 | 3008.73 | 0.715 | m |
| 50 | 3015.48 | 0.714 | m | m: means medium intensity
s: means strong intensity
vs: means very strong intensity.

Figure 6:
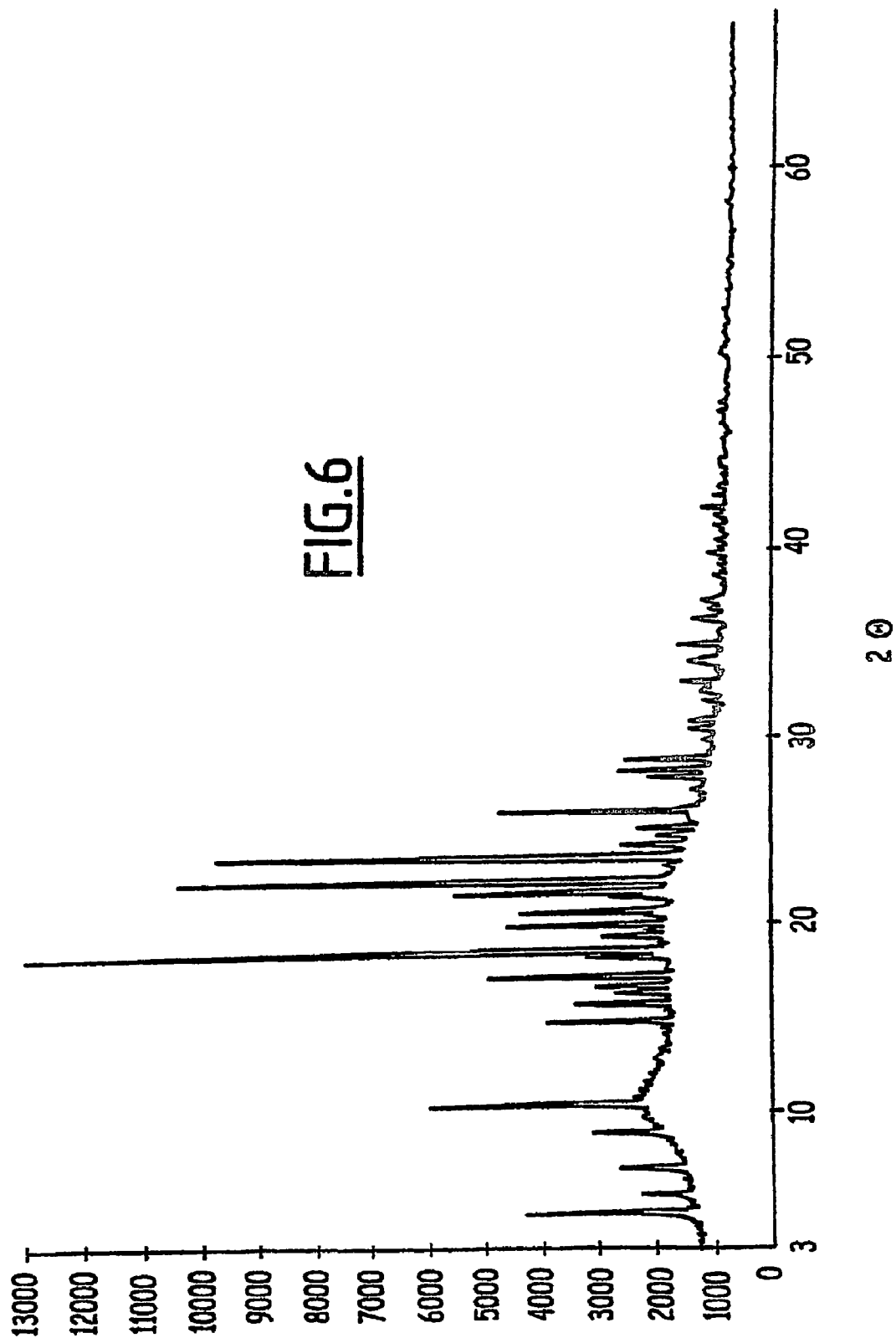
FIG. 6 represents an X-ray diffraction spectrum of the comparative compound of FIG. 4.

The X-ray diffraction spectrum of the stable form is shown in FIG. 6.

EXAMPLE 2

Preparation of the Metastable Form of 2E,4E-(methoxy-7-dimethyl-3-dihydro-2,3-benzoxepin-1-yl-5)-5-methyl-3-pentadien-2,4-oic Acid 0.335 l of aqueous 10 N sodium hydroxide solution (1.05 eq. of NaOH) is added with stirring, between 15 and 20° C., to a suspension of 1 kg of the stable form of 2E,4E-(methoxy-7-dimethyl-3,3-dihydro-2,3-benzoxepin-1-yl-5)-5-methyl-3-pentadien-2,4-oic acid, prepared in Example 1, suspended in 4 l of water, the solution thus obtained is filtered and the filter is rinsed with 0.5 l of water, which is combined with the filtrate. The filtrate is then added to a solution of 0.365 l of 37.5% sulfuric acid in 4 l of water preheated to between 80 and 85° C., 0.5 l of water is added, the mixture is then cooled to 25° C. and the precipitate thus formed is filtered off by suction. It is then rinsed three times with 2 l of water and then dried in a ventilated oven at 60° C.

Mass obtained: 0.99 kg
Yield: 99%
m.p.=155.4° C. (as measured on a Büchi machine)
HPLC analysis: purity of 99.7%.
FIG. 2 shows the infrared spectrum of the metastable form obtained.

The melting point of this metastable form is from 151 to 153° C. as measured by differential thermal analysis by scanning between 40 and 180° C. at a rate of 0.5° C./minute.

The curve obtained by differential thermal analysis is shown in FIG. 1.

The heat of fusion $\Delta_r H = 35.4$ kJ/mol.

Figure 2:
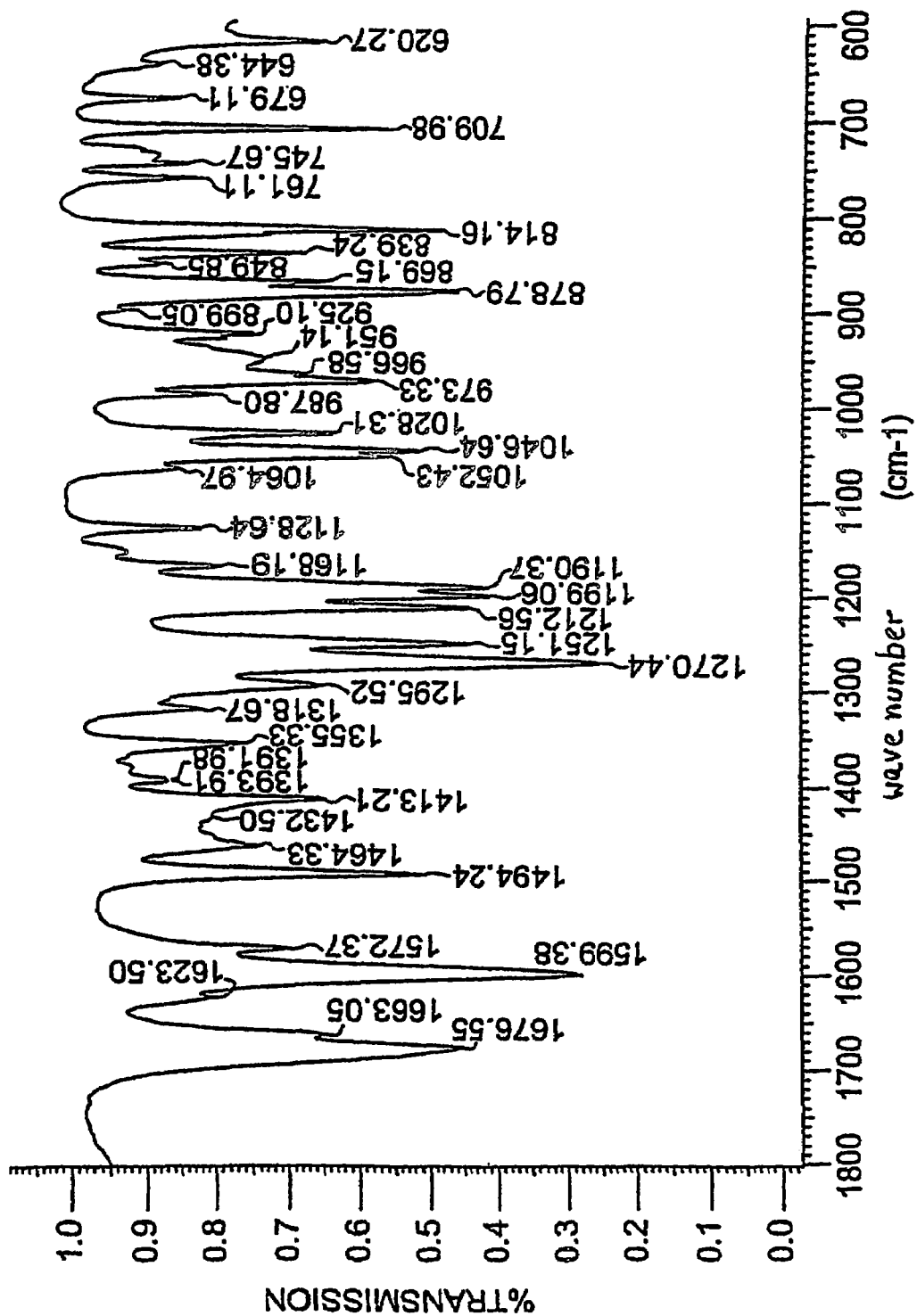
FIG. 2 represents an IR adsorption spectrum of the compound of FIG. 1.

The absorption wavelengths of the IR absorption spectrum shown in FIG. 2 are given in Table I presented above.

FIG. 3 shows the X-ray diffraction spectrum.

EXAMPLE 3

The advantages of the metastable form over the stable form are demonstrated in this example.

The dissolution kinetics promote the xenobiotic bioavailability of this type of active principle. It is also known that the dissolution kinetics are accelerated by increasing the specific surface area. A comparison of the apparent densities and specific surface areas of the two crystalline forms shows a greater apparent density of the metastable form compared with the thermodynamically stable form for the same specific surface area value. Table I below gives the respective values of the apparent density and the specific surface area (BET surface area) for the various crystalline forms.

However, increasing the specific surface area by reducing the mean particle size often gives rise to a reduction in the density.

Thus, the problem consists in formulating the active principle using a powder that is not very dense, this being particularly difficult in the case of presentation forms with a high dose of active principle. The use of the metastable form makes it possible to overcome this reduction in density caused by any type of grinding (such as that obtained by treatment in a knife mill or in a ball mill) and particularly for the purpose of micronisation. The metastable form thus shows a significant advantage in terms of pharmaceutical presentation.

TABLE I

Comparison of the specific surface area and the apparent density of the stable and metastable crystalline forms

| Crystalline form | Specific surface area or BET (m²/g) | Apparent density |
|---|---|---|
| stable | 0.4 | 0.29 |
| metastable | 2.8 | 0.30 |
| stable | 1.3 | 0.16 |
| stable | 1.5 | 0.18 |
| metastable | 3.1 | 0.30 |

In addition, comparative grinding studies, in particular by jet micronisation, were performed so as to obtain powders of the stable and metastable forms having the same specific surface area. These studies performed under similar operating conditions (feed pressure and grinding pressure) showed a greater specific surface area (BET) in the case of the metastable form. In other words, the metastable form was found to be more suitable for grinding or micronisation.

Table II below presents a comparison of the specific surface areas of different batches of the compound of the formula I in which n represents 1 and R in position 7 represents methoxy, obtained by carrying out different grinding conditions.

TABLE II

| Crystalline form | Batch No. | Grinding conditions | | Feed flow (kg/h) | BET (m²/g) |
|---|---|---|---|---|---|
| | | Feed Pressure (bar absolute) | Grinding pressure (bar absolute) | | |
| stable | 1 | 2.5 | 1.5 | very low | 7.3 |
| stable | 2 | 2.5 | 1.5 | 2.0 | 3.5 |
| stable | 3 | 2.5 | 1.5 | 0.8 | 4.8 |
| stable | 4 | 3.0 | 2.0 | 1.8 | 7.6 |
| stable | 5 | 3.3 | 2.3 | 2.5 | 8.4 |
| stable | 6 | 3.0 | 2.0 | 2.0 | 7.6 |
| metastable | 7 | 2.5 | 1.5 | 2.4 | 9.1 |
| metastable | 8 | 2.5 | 1.5 | 6.5 | 9.2 |
| metastable | 9 | 2.0 | 1.0 | 4.5 | 6.2 |
| metastable | 10 | 2.5 | 1.5 | 1.5 | 10.2 |
| metastable | 11 | 2.2 | 1.2 | 5.0 | 7.2 |

The invention claimed is:

1. A metastable form of a compound of formula I:

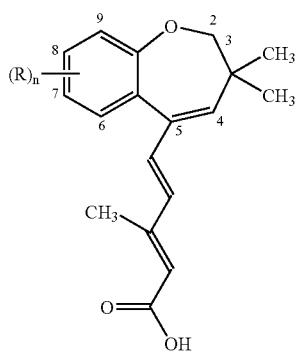

I in which n represents 1 and R, in position 7, represents methoxy, said metastable form having a melting point of 151 to 153° C. as measured by differential thermal analysis by scanning between 40 and 180° C. at a rate of 10° C./minute, and an X-ray diffraction spectrum defined by the absorption wavelengths in Table I below:

| No. | Absorption wavelength (cm-1) | Percentage of transmission (%) | Intensity |
|---|---|---|---|
| 1 | 620.27 | 0.660 | m |
| 2 | 844.38 | 0.892 | w |
| 3 | 679.11 | 0.865 | w |
| 4 | 709.98 | 0.568 | m |
| 5 | 730.24 | 0.907 | w |
| 6 | 736.03 | 0.891 | w |
| 7 | 745.67 | 0.849 | w |
| 8 | 761.11 | 0.843 | w |
| 9 | 814.16 | 0.518 | m |
| 10 | 839.24 | 0.683 | m; |
| 11 | 849.85 | 0.889 | w |
| 12 | 869.15 | 0.660 | m |
| 13 | 878.79 | 0.466 | s |
| 14 | 899.05 | 0.936 | w |
| 15 | 925.10 | 0.755 | m |
| 16 | 951.14 | 0.740 | m |
| 17 | 966.58 | 0.688 | m |
| 18 | 973.33 | 0.587 | m |
| 19 | 987.80 | 0.815 | w |
| 20 | 1028.31 | 0.641 | m |
| 21 | 1046.64 | 0.517 | m |
| 22 | 1052.43 | 0.562 | m |
| 23 | 1064.97 | 0.859 | w |
| 24 | 1128.64 | 0.825 | w |
| 25 | 1168.19 | 0.797 | w |
| 26 | 1190.37 | 0.422 | s |
| 27 | 1199.06 | 0.408 | s |
| 28 | 1212.56 | 0.441 | s |
| 29 | 1251.15 | 0.442 | s |
| 30 | 1270.44 | 0.254 | s |
| 31 | 1295.52 | 0.659 | m |
| 32 | 1318.67 | 0.825 | w |
| 33 | 1355.33 | 0.769 | w |
| 34 | 1391.98 | 0.872 | w |
| 35 | 1393.91 | 0.872 | w |
| 36 | 1413.21 | 0.651 | m |
| 37 | 1432.50 | 0.806 | w |
| 38 | 1464.33 | 0.743 | m |
| 39 | 1494.24 | 0.511 | m |
| 40 | 1572.37 | 0.707 | m |
| 41 | 1599.38 | 0.284 | s |
| 42 | 1623.50 | 0.810 | w |
| 43 | 1663.05 | 0.650 | m |
| 44 | 1676.55 | 0.458 | s |
| 45 | 2837.99 | 0.863 | w |
| 46 | 2871.75 | 0.847 | w |
| 47 | 2934.45 | 0.819 | w |
| 48 | 2960.50 | 0.818 | w |
| 49 | 3018.38 | 0.898 | w | in which
w means weak intensity,
s means strong intensity, and m
means medium intensity.

2. A process for obtaining the metastable form of a compound of formula I according to claim 1 comprising:
   a) forming a carboxylic acid salt of the corresponding stable form of a compound of the formula I;
   b) acidifying an aqueous solution of the salt obtained after step a) until precipitation of the carboxylic acid in its metastable form is obtained.

3. The process according to claim 2, wherein, in a sodium or potassium salt is formed.

4. The process according to claim 2, wherein, in a), the stable form of the compound of the formula I is reacted with potassium hydroxide or sodium hydroxide.

5. The process according to claim 2, wherein, in a), the process is performed in aqueous medium, the stable form of the compound of the formula I initially being in suspension in water.

6. The process according to claim 5, wherein, in b), the acidification is performed by the action of hydrochloric acid or sulfuric acid.

7. The process according to claim 5, wherein acidification in b) is performed by adding hydrochloric acid or sulfuric acid to the reaction medium.

8. The process according to claim 2, wherein, in b) acidification is performed with an acid having a concentration between 0.05 M and 10 M.

9. The process according to claim 2, wherein, in b), the acidification is performed at between 50 and 120° C., and precipitation is performed by cooling the reaction medium.

10. The process according to claim 9, wherein precipitation is performed by cooling the reaction medium to between 15 and 40° C.

11. The process according to claim 2, wherein the stable form of the compound of the formula I is obtained by saponification of the corresponding alkyl ester, followed by acidification, extraction with a water-immiscible solvent, separation of the phases by settling, evaporation and then crystallisation from a solvent which is a lower alkanol, acetonitrile, ethyl acetate, tetrahydrofliran or acetone.

12. A pharmaceutical composition comprising a therapeutically effective amount of the metastable form of a compound of the formula I according to claim 1, in combination with a pharmaceutically acceptable excipient.

13. A method for the treatment of dyslipidaemia, atherosclerosis or diabetes, comprising administering a compound according to claim 1.

14. The process according to claim 2, wherein, in b) acidification is performed with an acid having a concentration between 0.1 and 0.5 M.

* * * * *

UNITED STATES PATENT AND TRADEMARK OFFICE
CERTIFICATE OF CORRECTION

PATENT NO.        : 7,470,719 B2
APPLICATION NO.   : 10/530571
DATED             : December 30, 2008
INVENTOR(S)       : Nathali Bosc et al.

It is certified that error appears in the above-identified patent and that said Letters Patent is hereby corrected as shown below:

Title Page; item (54); Title: line 3, reads "DYSLIPIDAEMIA A THEROSCLEROSIS" should read -- DYSLIPIDAEMIA, ATHEROSCLEROSIS --

Title Page; item (75); Inventors: line 3, reads "Boudet" should read -- Pithiviers --

Column 10, line 31, insert line break after "intensity, and" and remove the line break between "m" and "means"

Column 10, line 37, reads "formula I;" should read -- formula I by forming a carboxylic acid salt; --

Column 10, line 43, reads "wherein, in a)" should read -- wherein in a) --

Column 11, line 4, reads "tetrahydrofliran" should read -- tetrahydrofuran --

Signed and Sealed this

Twenty-ninth Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,470,719 B2  Page 1 of 1
APPLICATION NO. : 10/530571
DATED : December 30, 2008
INVENTOR(S) : Nathali Bosc et al.

It is certified that error appears in the above-identified patent and that said Letters Patent is hereby corrected as shown below:

Title Page; item (54); Title: line 3, and Column 1, line 3, reads "DYSLIPIDAEMIA A THEROSCLEROSIS" should read -- DYSLIPIDAEMIA, ATHEROSCLEROSIS --

Title Page; item (75); Inventors: line 3, reads "Boudet" should read -- Pithiviers --

Column 10, line 31, insert line break after "intensity, and" and remove the line break between "m" and "means"

Column 10, line 37, reads "formula I;" should read -- formula I by forming a carboxylic acid salt; --

Column 10, line 43, reads "wherein, in a)" should read -- wherein in a) --

Column 11, line 4, reads "tetrahydrofliran" should read -- tetrahydrofuran --

This certificate supersedes the Certificate of Correction issued September 29, 2009.

Signed and Sealed this

Twenty-seventh Day of October, 2009

David J. Kappos
*Director of the United States Patent and Trademark Office*